United States Patent
Mizuno

(10) Patent No.: US 6,939,292 B2
(45) Date of Patent: Sep. 6, 2005

(54) CAPSULE TYPE ENDOSCOPE

(75) Inventor: Hitoshi Mizuno, Koganei (JP)

(73) Assignee: Olympus Corporation, Tokyo (JP)

(*) Notice: Subject to any disclaimer, the term of this patent is extended or adjusted under 35 U.S.C. 154(b) by 201 days.

(21) Appl. No.: 10/173,998

(22) Filed: Jun. 18, 2002

(65) Prior Publication Data

US 2002/0198439 A1 Dec. 26, 2002

(30) Foreign Application Priority Data

Jun. 20, 2001 (JP) ........................................ 2001-186827

(51) Int. Cl.⁷ ................................................ A61B 1/05
(52) U.S. Cl. ........................ 600/118; 600/160; 600/109; 600/117; 600/476
(58) Field of Search ................................. 600/109, 101, 600/160, 118, 300, 117, 476; 348/65, 74, 76

(56) References Cited

U.S. PATENT DOCUMENTS

| 5,604,531 | A | | 2/1997 | Iddan et al. | |
|---|---|---|---|---|---|
| 6,036,637 | A | * | 3/2000 | Kudo | 600/173 |
| 6,233,476 | B1 | * | 5/2001 | Strommer et al. | 600/424 |
| 6,240,312 | B1 | * | 5/2001 | Alfano et al. | 600/476 |
| 6,324,418 | B1 | * | 11/2001 | Crowley et al. | 600/476 |
| 6,632,175 | B1 | * | 10/2003 | Marshall | 600/309 |
| 6,709,387 | B1 | * | 3/2004 | Glukhovsky et al. | 600/109 |
| 2001/0051766 | A1 | * | 12/2001 | Gazdzinski | 600/309 |
| 2002/0099310 | A1 | * | 7/2002 | Kimchy et al. | 600/587 |
| 2002/0109774 | A1 | * | 8/2002 | Meron et al. | 348/74 |
| 2002/0165592 | A1 | * | 11/2002 | Glukhovsky et al. | 607/62 |
| 2003/0028078 | A1 | * | 2/2003 | Glukhovsky | 600/109 |
| 2003/0117491 | A1 | * | 6/2003 | Avni et al. | 348/77 |
| 2003/0167000 | A1 | * | 9/2003 | Mullick et al. | 600/424 |
| 2003/0174208 | A1 | * | 9/2003 | Glukhovsky et al. | 348/131 |
| 2003/0208107 | A1 | * | 11/2003 | Refael | 600/300 |
| 2003/0214579 | A1 | * | 11/2003 | Iddan | 348/81 |
| 2004/0073087 | A1 | * | 4/2004 | Glukhovsky et al. | 600/109 |

FOREIGN PATENT DOCUMENTS

JP 1-305925 12/1989

* cited by examiner

*Primary Examiner*—John P. Leubecker
(74) *Attorney, Agent, or Firm*—Scully, Scott Murphy & Presser

(57) ABSTRACT

A capsule-type endoscope comprising a capsule body, an image pickup element, illuminating elements, an image signal processing circuit, a memory, an image information transmitting circuit and an antenna for wireless transmission. The capsule body contains the pickup element, the illuminating elements, the processing circuit, the memory, transmitting circuit and the antenna. While the capsule body remains in a living body, the image pickup element takes images of an interior of the living body. The processing circuit processes the image, generating image information. The memory stores the information. The transmitting circuit reads the information and supplies it to the antenna. The antenna transmits the information by radio, from the living body.

10 Claims, 5 Drawing Sheets

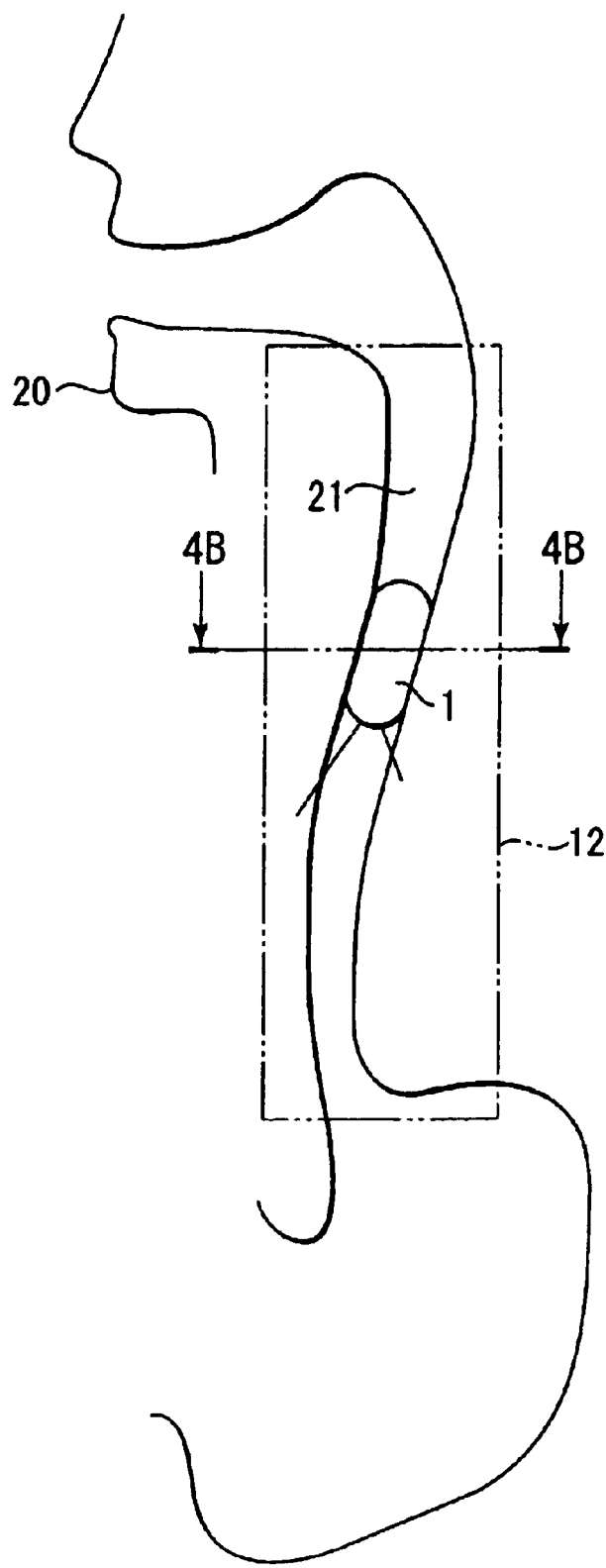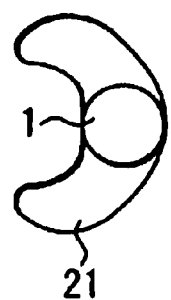
FIG. 4B
FIG. 4A

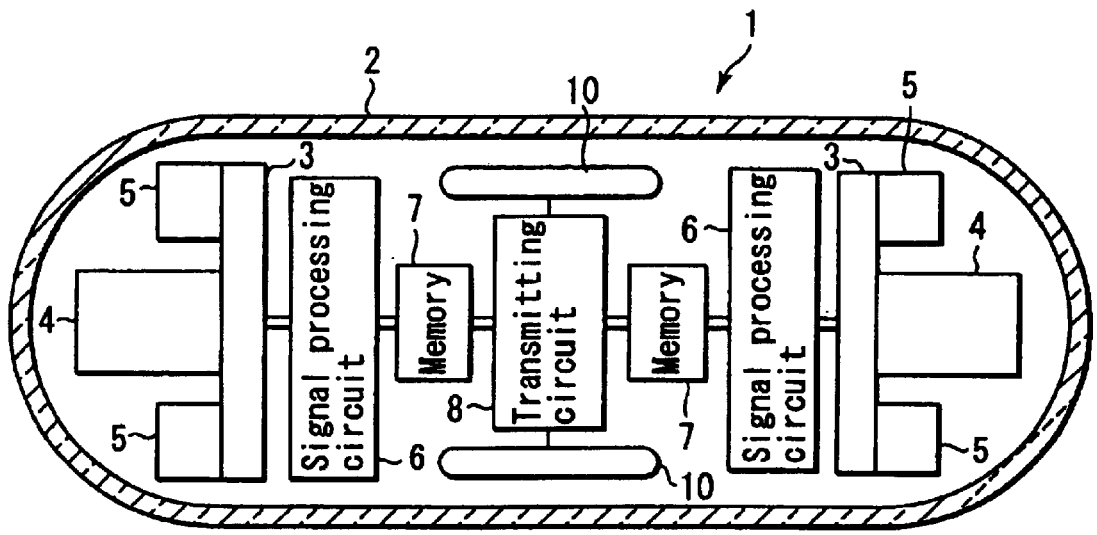
FIG. 9
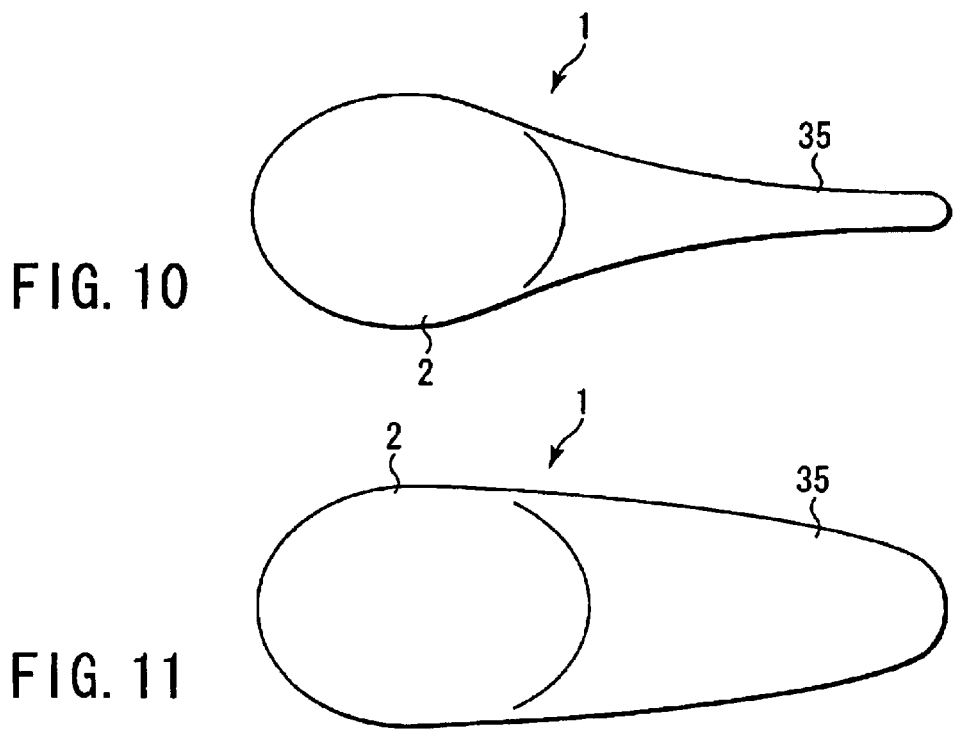
FIG. 10
FIG. 11

CAPSULE TYPE ENDOSCOPE

CROSS-REFERENCE TO RELATED APPLICATIONS

This application is based upon and claims the benefit of priority from the prior Japanese Patent Application No. 2001-186827, filed Jun. 20, 2001, the entire contents of which are incorporated herein by reference.

BACKGROUND OF THE INVENTION

1. Field of the Invention

The present invention relates to a capsule type endoscope having a capsule body internally equipped with an image taking device for taking images in the body cavity of a human subject.

2. Description of the Related Art

An endoscope can be inserted into the esophageal canal of the human subject to directly examine the inner wall of any affected region of interest with high reliability. However, this method needs relatively large equipment and, in addition, a large burden is inflicted on the patient and operator. Therefore, such conventional endoscopy is hard to adopt in a first screening such as mass screening.

As a first screening such as mass screening, in general, it is usually only necessary to examine the presence or absence of any affected region of interest at least, and a simpler examination should be adopted from the standpoint of reduced cost, pain and psychological unrest.

Therefore, it has been desired to establish simpler checking means for adopting a first screening program by which it is possible to directly and exactly check the esophageal wall for any affected new region of interest.

One approach is directed to a camera type of system according to which an endoscope is formed as a capsule configuration and, by swallowing such a capsule, images are taken by that camera-incorporated capsule during its passage through the esophageal canal to allow the corresponding image signals to be, for example, wirelessly transmitted to the outside in realtime.

However, upon image transmission in realtime, the video frame rate is normally very slow at two frames per second, while, on the other hand, the time during which the capsule passes through the esophageal canal is very short, being of the order of one second. As a result, only about one or two frames can be obtained during the passage of the capsule through the esophageal canal. Therefore, adequate reliability can not be ensured at such a frame rate and hence it is not suitable for the examination of the esophagus. Further, there has been some inconvenience in that exact examination of not only the esophagus but also the internal organs such as the stomach, the duodenum the small intestine and the large intestine can not be made for any affected region of interest or its neighborhood.

BRIEF SUMMARY OF THE INVENTION

It is accordingly the object of the present invention to provide a capsule type endoscope which can take many more frames of images for a shorter period in which the capsule passes through an affected region or its neighborhood, or a region of interest, of the esophageal canal and internal organs.

In order to achieve the above object, there is provided a capsule type endoscope of the present invention having a capsule body comprising an illuminating unit configured to illuminate the inside of a living body, an image pickup element configured to take images in a living body illuminated by the illuminating unit and generate taken image signals, a processing circuit configured to process the taken image signals to generate image signals, a memory configured to store the image signals, a transmitting circuit configured to take out the image signals from the memory and convert these image signals to transmission signals, and an antenna configured to wirelessly transmit these transmission signals to the outside of the living body, wherein the image signals generated from the processing circuit are stored in the memory, the image signals stored in the memory are converted to transmission signals by the transmitting circuit and the transmission signals are wirelessly transmitted to the outside by the antenna.

It is, therefore, possible to take many more frames of images in a shorter period of time during which the capsule passes through the esophageal canal and obtain added reliability on examination.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 4A is an explanatory view showing the capsule type endoscope in use which is based on the first embodiment of the present invention;

FIG. 4B is a transverse cross-sectional view as taken along line 4B—4B in FIG. 4A;

FIG. 9 is a view in longitudinal cross-section diagrammatically showing a capsule type endoscope according to a fifth embodiment of the present invention;

FIG. 10 is a side view showing a capsule type endoscope according to a sixth embodiment of the present invention; and FIG. 11 is a plan view showing the capsule type endoscope according to the sixth embodiment of the present invention.

DETAILED DESCRIPTION OF THE INVENTION (First Embodiment)

A capsule type endoscope according to a first embodiment of the present invention will be described below by referring to FIGS. 1 to 5.

Figure 1:
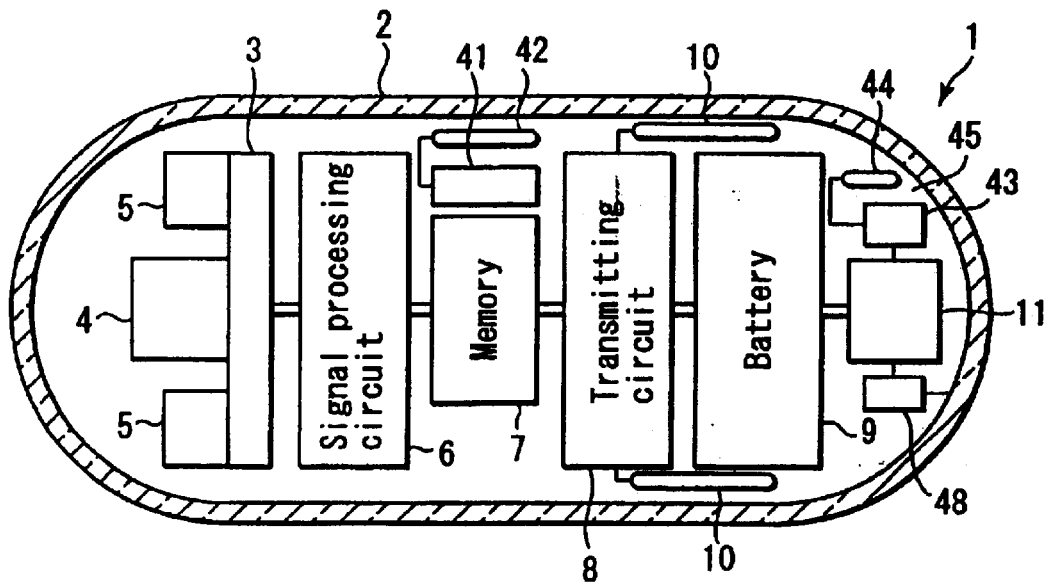
FIG. 1 is a view in longitudinal cross-section diagrammatically showing a capsule type endoscope according to a first embodiment of the present invention.

FIG. 1 is a diagrammatic view showing a capsule type endoscope 1 configured as a so-called compact camera. The endoscope has a light-transparent capsule body 2 serving as a protective outer shell. The capsule body 2 is formed as a case having such an outer configuration and size that it can be passed through the esophageal canal upon being swallowed via the mouth. A sealed storage chamber is created within the capsule body 2. As shown in FIG. 1, the capsule body 2 has a cylindrical intermediate section axially elongated compared with its diameter. Both the opposite end sections of the capsule body 2, are each formed to have an axially outwardly extending hollow semispherical configuration with at least its outer surface smoothly formed. Since the capsule body 2 is formed as being axially elongated compared with the diameter, it can be easily swallowed and the swallowing movement direction is readily liable to be guided toward the axial direction of the capsule body 2.

As shown in FIG. 1, various kinds of associated component parts are incorporated within the storage chamber of the capsule body. Within the capsule body 2 are stored a substrate 3, an image taking device having an image pickup element 4 and illuminating elements 5 mounted on the substrate, an image (video) signal processing circuit 6, a memory 7, an image (video) signal transmitting circuit 8, a battery 9, an antenna 10, a position detecting means 11, etc.

Figure 2:
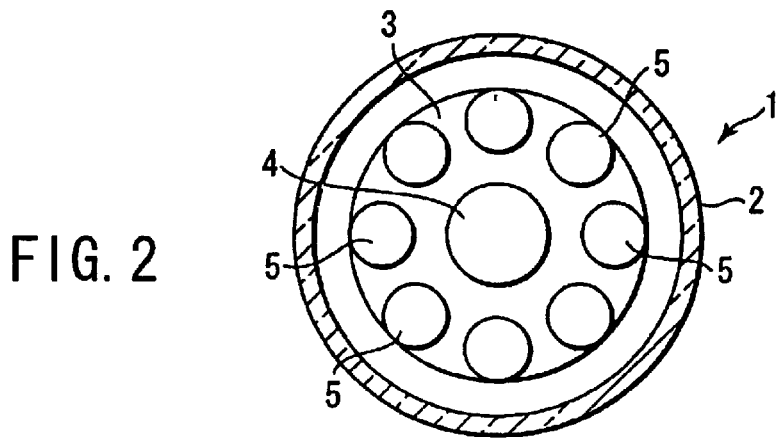
FIG. 2 is a view in transverse cross-section diagrammatically showing a capsule type endoscope according to the first embodiment of the present invention.

As the image pickup element 4 use is made of a solid state image pickup element such as a C-MOS and a CCD. As the illuminating elements 5 use is made of, for example, LEDs and so on. As shown in FIG. 2, the illuminating elements 5 are equidistantly arranged around the image pickup element 4. Each illuminating light emitted from the corresponding illuminating element 5 is radiated onto an image taking field through a transparent end wall of the capsule body 2 to illuminate the image taking field. The image pickup element 4 takes images in the illuminated image taking field.

The image signal processing circuit 6 processes signals taken by the image taking element 4 in the image taking device to generate image signals. The signals are supplied to a memory 7 where these signals are once stored. The stored image signals are sequentially taken out by the image signal transmitting circuit 8 and sequentially converted to transmission signals. The transmission signals are sequentially transmitted via the antenna 10 to the outside by wireless. The battery 9 is used as a power source for each element, circuits and so on.

The position detecting means 11 has a sensor for detecting an electromagnetic field at its site and detects the position of the capsule body 2 by the electromagnetic field detected by the sensor. For example, it responds to an external plate 12, such as a magnetic plate or conductive plate, as will be set out below to detect the external plate 12 and decides its own position. Further, it may be made to respond to an electromagnetic field generated in a magnetic coil if the external plate placed outside the living body is replaced by the magnetic coil.

Figure 3:
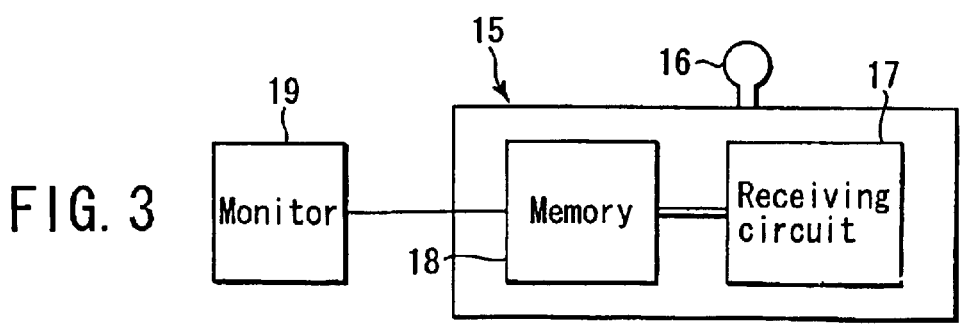
FIG. 3 is a diagrammatic view showing a receiver installed outside a living body relative to the first embodiment of the present invention.
Figure 5:
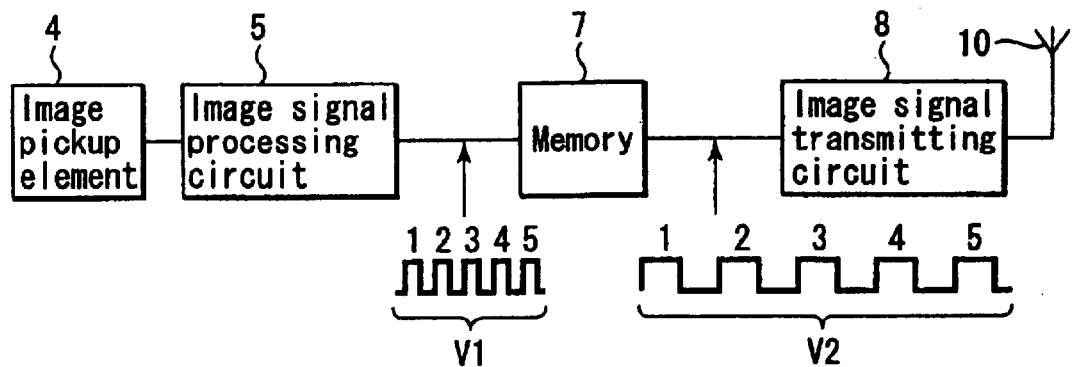
FIG. 5 is an explanatory view showing a circuit arrangement of the capsule type endoscope according to the first embodiment of the present invention.

FIG. 3 shows a receiver 15 located outside the living body. The receiver 15 receives/records image signals sent by a wireless transmission from the capsule type endoscope 1. The receiver 15 includes a receiving antenna 16, an image signal receiving circuit 17 and an image recording means (memory) 18. The image signals received by the image signal receiving circuit 17 are recorded in the image recording means 18. The image recording means 18 transmits the image signals to a monitor 19 where these images are monitored. The images taken can also be transmitted to a given image receiver at a remote site via a communication means such as the Internet (not shown).

It is to be noted that a program capable of a variable setting is provided for the image pickup element 4, image information transmitting circuit 8, image signal processing circuit 6 and memory 7. The image taking rate by the image pickup element 4, the transmission rate by the image information transmitting circuit 8, the timing and time for allowing the storing of the image signals into the memory 7 through the image signal processing circuit 6 are arbitrarily set or variable by being programmable. These may be settable or variable even in such cases as to varying the program of a timer, etc., in the capsule body 2 before swallowing the capsule body 2, to vary a program by information from outside the living body after the capsule body 2 has been swallowed, or to vary both. In this case, a receiver 41 and antenna 42 are provided in the capsule body 2 as shown in FIG. 1 to receive information for instructing a variation of the information contents.

Now, an explanation will be made below about how to use the capsule type endoscope 1 set out above. First, as shown in FIG. 4A, the external plate 12 is positioned in a manner to correspond to the esophageal canal 21 of a patient 20 and it is located on the external surface of the patient 20.

After this, the capsule type endoscope 1 is swallowed via the mouth with its axial direction guided toward the swallowing movement direction.

As shown in FIG. 4A, the capsule type endoscope 1 passes through the esophageal canal 21 with its longitudinal axis direction guided toward the longitudinal direction of the esophageal canal 21. When the capsule type endoscope 1 passes through the esophageal canal 21, the position detecting means 11 of the capsule type endoscope 1 senses the external plate 12 and the image taking device starts its operation. The position detecting means 11, while sensing the external plate 12, decides that the capsule type endoscope 1 is situated in the esophageal canal 21.

As shown in FIGS. 4A and 4B, while the capsule endoscope 1 is detected as being situated in the esophageal canal 21, the illuminating elements 5 are lit and the image taking device is intermittently operated. The area of the esophageal canal 21 thus illuminated is thereby imaged by the image pickup element 4 many number of times.

The capsule type endoscope 1 can pass through the esophageal canal 21, usually within a very short time of one second. During this short time, the image pickup element 4 takes many frames of an image at high speeds, while scanning the entire area of the esophageal canal 21. The minimum frame rate required for continuously scanning the entire area of the esophageal canal 21 is 5 frames/second. Assume that the canal 21 is 30 cm long as in most cases, that the focal depth of the endoscope 1 is 6 cm and that it takes the endoscope 1 one second to pass the canal 21. Then, the minimum frame rate is given as:

$$30(cm)/6(cm)/1(sec)=5 \text{ frames/second}$$

The length of the esophageal canal varies from person to person, and the focal depth of the endoscope 1 may change from time to time. If the endoscope 1 needs 0.5 seconds to pass through the canal 21, the focal depth of the endoscope 1 is 1 cm, and 30 frames (=30(cm)/1(cm)) must be taken, then the frame rate should be 60 frames/second.

However, if the frame rate is less than 5 frames/second, for example 2 frames/second, it is not easy to set the focal depth at 10 cm or more. It is therefore hard to set the far point at 10 cm or more for tubular organs such as the esophageal canal. Consequently, it would be difficult to observe the esophageal canal continuously. However hard the patient tries, he or she cannot swallow the capsule to move it continuously and slowly through the entire esophageal canal. In view of this, the imaging of the canal must be carried out at a frame rate of at least 5 frames/second to achieve continuous observation of the entire area of the esophageal canal 21.

Further, the image signal processing circuit 6 sequentially processes those signals taken by the image pickup element 4 to generate image signals, and these image signals are stored in the memory 7 in realtime. For example, an image of a hundred thousand pixels is compressed under the JPEG system and those images corresponding to 30 frames are sequentially retained in the memory 7. Here, recording rate at which the generated image signal is stored in the memory 7 in realtime is given by V1.

After the capsule type endoscope has dropped past the esophageal canal 21 into the stomach, the image taking operation is stopped because the position detecting means 11 ceases to detect the external plate 12. Thus, the capsule type endoscope 1 performs a high-speed image taking operation only during the time in which it passes through the esophageal canal. Since the capsule type endoscope stops its image taking operation after it has dropped into the stomach and does not continue its image taking operation, the capacity of the memory 7 can be effectively utilized without wasting it. Further, the remaining capacity of the memory 7 can be kept for another image taking operation.

Although the signals of those images taken by the image pickup element 4 of the image taking device have been once stored in the memory 7, the image information items are sequentially read out of the memory 7 and wirelessly transmitted by the image signal transmitting circuit 8 to the outside of the living body via the antenna 10. The operation of storing the signals of the images taken by the image pickup element 4 is continued without waiting for the completion of the transmission of the previous image information items by the image signal transmitting circuit 8 and these are sequentially stored in the memory 7.

Incidentally, the transmitting speed V2 by the image signal transmitting circuit 8 is as slow as a frame rate of two frames/second. However, the signals of the images taken by the image taking element 4 continue their storing operation relative to the memory 7 without waiting for the completion of the transmission operation. That is, since the image signal taking operation while allowing the transmitting operation is continued, a larger amount of image signals can be stored in the memory 7. Even if the transmitting rate V2 is slower than the recording rate V1, it is possible to make the recording rate V1 fairly rapid.

Further, the image signals stored in the memory 7 are wirelessly transmitted by the image signal transmitting circuit 8 to the outside of the living body via the antenna 10 in the order in which these image signals are stored.

The operation of storing the image signals into the memory 7 and the transmitting operation by the image signal transmitting circuit 8 are carried out individually. A greater amount of image signals is stored for a shorter time period into the memory 7 and the image signals stored in the memory 7 are sequentially transmitted by the image signal transmitting circuit 8 to the outside of the living body in a wireless fashion.

On the other hand, the receiver 15 externally installed as shown in FIG. 3 receives the image signals via the receiving antenna 16 which are transmitted from the capsule type endoscope 1 and the image signals are recorded via the image signal receiving circuit 17 into the image recording means 18. Further, the image signals are transmitted to the monitor 19 where these images are monitored or to an image receiver at a remote site through a communication means such as the Internet (not shown).

The position detecting means 11 as set out above detects the position of the capsule body 2, and the image taking time, the times of image taking, and so on, are controlled. By doing so it is possible to adopt various kinds of image taking modes. For example, when the capsule body passes through the position corresponding to the external plate 12, images are taken at a frame rate of 60 frames/second and, after the passage of the capsule body past that corresponding position, switching is made to a mode in which images are obtained at a frame rate of 2 frames/second. By doing so, proper image taking is carried out in accordance with each site.

Although, in the above-mentioned embodiment, the position detecting means 11 detects the external plate 12 to decide a position corresponding to the location of the capsule type endoscope 1, this invention is not restricted thereto and it is also possible to decide the position of the capsule type endoscope with the use of other position detecting systems. Further, the position detecting means as set out above may be comprised of a gyro, an acceleration sensor, a sensor for detecting the moving speed of the capsule body 2, and so on.

Further, the position detected by the position detecting means 11 may be stored as position information in the memory 43 and the position information may be wirelessly transmitted to the outside by the transmitting unit 45 including an antenna 44. Still further, an adjusting unit 48 may be provided for adjusting the image taking rate by the image pickup element 4, the ON/OFF operation of the image taking, and so on, according to the position information of the capsule body 2 detected by the detecting means 11 as shown in FIG. 1.

(Second Embodiment)

Figure 6:
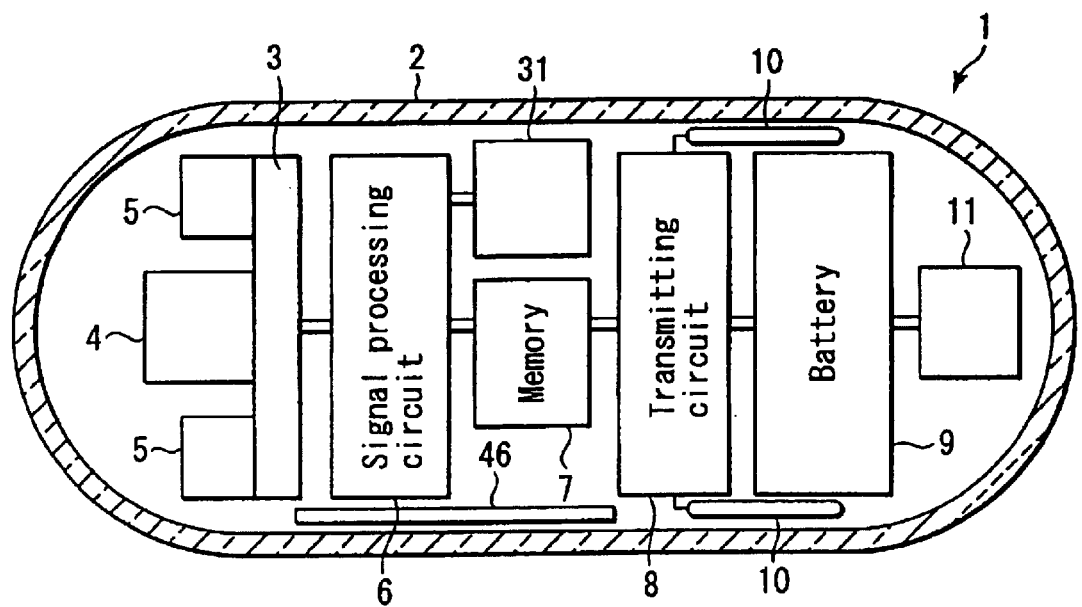
FIG. 6 is a view in longitudinal cross-section diagrammatically showing a capsule type endoscope according to a second embodiment of the present invention.

An explanation will be made below about a capsule type endoscope according to a second embodiment of the present invention by referring to FIG. 6. The capsule type endoscope 1 of this invention includes a built-in timer 31 in a capsule body 2, and, by means of this timer 31, the image taking time and the times of image taking by an image taking device, and so on, are controlled based both on its time data and according to a timer program. The remaining structure is the same as that of the first embodiment.

Based on the time data of the timer 31 and according to the timer program, the image taking time, the times of image taking, and so on, can be controlled and, by doing so, various modes of image taking can be adopted. For example, the capsule type endoscope 1, after being passed through the esophageal canal 21, is discharged via the anus past the stomach, the small intestine and the large intestine but it takes a whole day and night, unlike the passage of the capsule type endoscope through the esophageal canal, to move the capsule type endoscope through the stomach, the small intestine and the large intestine. For this reason, the image taking rate is varied or ON/OFF operated according to a schedule initially set by the timer 31 and, by doing so, it is possible to effectively utilize a data retaining capacity in the memory 7 and also to reduce the wastage of the battery 9 for lighting illuminating means. An image taking examination can be made over the whole alimentary canal, including a gastrointestinal image taking examination after the capsule type endoscope has passed through the esophageal canal 21.

(Third Embodiment)

Figure 7:
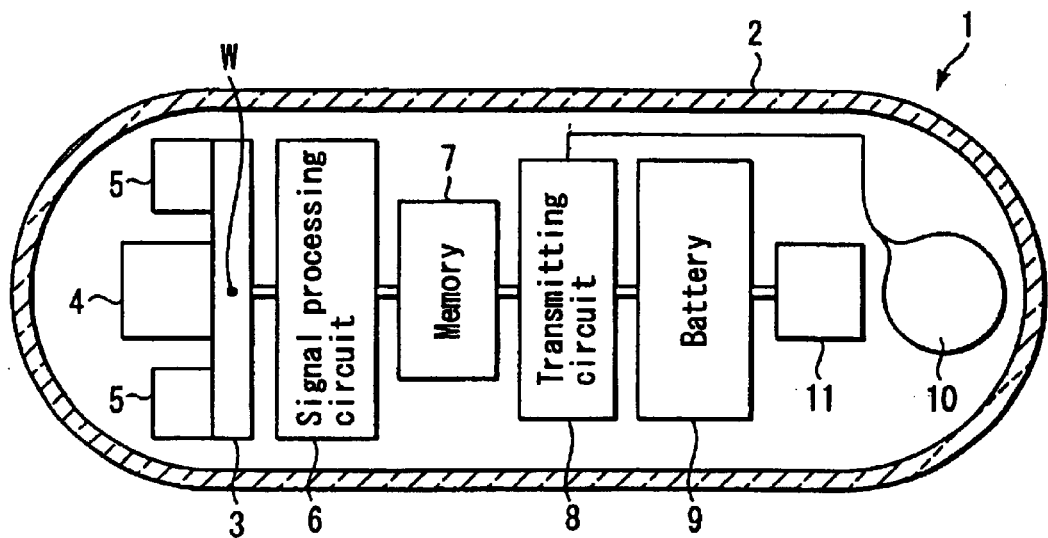
FIG. 7 is a view in longitudinal cross-section diagrammatically showing a capsule type endoscope according to a third embodiment of the present invention.

An explanation will be made below about a capsule type endoscope according to a third embodiment of the present invention by referring to FIG. 7. In the capsule type endoscope 1 according to this embodiment, the center of gravity, W, is located at or near a position corresponding to the image pickup element 4. Here, it is located on a longitudinal axis of the capsule body 2 at a position where the substrate 3 is situated. That is, the center of gravity, W, of the capsule type endoscope 1 is located at a forward site of the capsule body 2 on the image pickup element 4 side. The position of gravity, W is determined depending upon the shape and material of the capsule body 2 as well as the size and number of built-in component parts and their locations, and so on, and it is determined from the standpoint of these design considerations.

Since the center of gravity, W, of the capsule type endoscope 1 is located at the forward site of the capsule body 2 on the image pickup element 4 side, the capsule type endoscope 1 is easier to swallow and, after being swallowed, the direction of the capsule body 2 is stably guided and it is possible to stably and positively take images in the esophageal canal.

(Fourth Embodiment)

Figure 8:
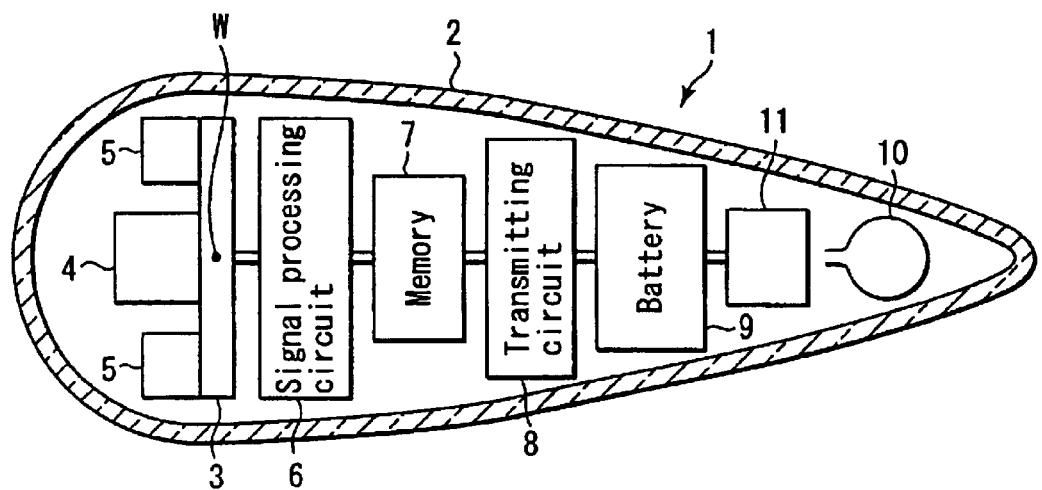
FIG. 8 is a view in longitudinal cross-section diagrammatically showing a capsule type endoscope according to a fourth embodiment of the present invention.

An explanation will be made below about a capsule type endoscope according to a fourth embodiment of the present invention by referring to FIG. 8. In the capsule type endoscope 1 of the fourth embodiment, its capsule body 2 is so formed as to have a semi-spherical configuration at the forward end section as viewed from its longitudinal direction and the backward end section of the capsule body 2 is so formed as to be gradually tapered toward a backward direction. The forward end section of the capsule body 2 is larger in diameter than the backward end section. If the capsule body 2 is made thicker on the forward end side, then the center of gravity, W, of the capsule type endoscope 1 tends to be located toward the forward section of the capsule body 2. Since the capsule body 2 has such a shape as set out above, it is easier to swallow toward a predetermined direction.

(Fifth Embodiment)

An explanation will be made below about a capsule type endoscope according to a fifth embodiment of the present invention by referring to FIG. 9. In the capsule type endoscope 1 according to this embodiment, its capsule body 2 is so formed as to have image taking devices incorporated at opposite longitudinal end portions. By so doing it is possible to take images at both the longitudinal forward and backward sections of the capsule body 2. The respective image taking device is so formed as to have its corresponding image pickup element 4 and illuminating elements 5 mounted on a corresponding substrate 3.

According to the thus structured capsule type endoscope 1, when the capsule body 2 is swallowed, it is possible to take images not only at its forward section but also at its backward section as viewed in its moving direction and, hence, to take more images corresponding to more sites of interest. In addition, it is also possible to take images corresponding to the inner wall sites of the esophageal canal from different directions. As a result, more reliability is ensured on diagnosis.

Since the backward sites can be taken as images when the capsule body 2 is swallowed, it is possible to take images at an important region of interest just at or near the exit opening of the esophagus into the stomach, in particular, immediately before, and just at the moment of, the dropping of the capsule body 2 into the stomach.

(Sixth Embodiment)

An explanation will be made below about a capsule type endoscope according to a sixth embodiment of the present invention by referring to FIGS. 10 and 11. In the capsule type endoscope 1 of this embodiment, a capsule body 2 has a soft flat tail 35 at its backward portion.

According to the capsule type endoscope 1 having such a tail 35, the capsule body 2 is easier to swallow and, when the capsule type endoscope 1 has been swallowed, the direction of the capsule body 2 is stably oriented by the tail 35 and it is possible to positively take images of the inner wall of the esophageal canal.

It is to be noted that the present invention set out above is not restricted to the above-mentioned respective embodiments and can be applied to other modes of application. Although, in the above-mentioned embodiments, the explanation has been made more about taking images of the inner wall of the esophageal canal, the object of the image taking is not restricted to the esophagus and the present invention can be applied to image taking of a region of interest to examine not only the esophagus but also those organs such as the stomach, the small intestine and the large intestine for any affected region of interest and its neighborhood. In this case, it is only necessary to set the position of the position detecting means and program of the timer to the region of interest.

The present invention is not limited to the capsule type endoscope described above, which has a battery in the capsule body to supply power to the elements and circuits provided in the endoscope. Rather, the invention may be applied to a capsule type endoscope shown in FIG. 6, in which a power receiver 46 is provided in the capsule body 2. The receiver 46 continuously receives power that is supplied from the outside in the form of electromagnetic waves, for example, microwaves or light that passes through the living tissues and organs. Further, a battery may be provided for storing electric power received by the power receiver 46 or may be made rechargeable. According to such a structure, the electric power can be continuously supplied in a contactless way from outside to the capsule type endoscope in a living body and there is the advantage that the capsule type endoscope in the living body can be positively operated for a long time. Stated in more detail, the capsule body has a built-in power receiving means such as a power receiving antenna or a solar cell unit and, outside the living body, a power transmitting antenna or light emitting means as a light emitting plate/light emitting unit is arranged toward the inside of the living body.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A capsule type endoscope comprising:
   a capsule body comprising a forward part and a rearward part with respect to a direction in which a subject swallows the capsule body, the forward part having a larger diameter than the rearward part, the capsule body further having a soft flat tail at the rearward part;

an illuminating unit provided in the capsule body and configured to illuminate an inside of a living body;

an image pickup element provided in the capsule body and configured to take images in a living body illuminated by the illuminating unit and to generate signals from the images taken;

a processing circuit provided in the capsule body and configured to process the signals, thereby to generate image signals;

a memory provided in the capsule body and configured to store the image signals;

a transmitting circuit provided in the capsule body and configured to read the image signals from the memory and convert the image signals to signals to be transmitted;

an antenna configured to transmit the transmit signals from the living body, without using wires; and a timer configured to set an operation schedule, wherein the image pickup element, image processing circuit, memory, transmitting circuit and antenna operate in accordance with the operation schedule set by the timer.

2. A capsule type endoscope comprising:

a capsule body;

an illuminating unit provided in the capsule body and configured to illuminate an inside of a living body, an image pickup element provided in the capsule body and configured to take images in a living body illuminated by the illuminating unit and to generate signals from the images taken;

a processing circuit provided in the capsule body and configured to process the signals, thereby to generate image signals;

a memory provided in the capsule body and configured to store the image signals, a transmitting circuit provided in the capsule body and configured to read the image signals from the memory and convert the image signals to be transmitted;

an antenna configured to transmit the signals from the living body, without using wires;

a detecting unit which is held in the capsule body and which detects a position of the capsule body, and an adjuster for adjusting an image taking rate of the image pickup element, in accordance with the position of the capsule body which has been detected by the detecting unit.

3. A capsule type endoscope according to claim 2, further comprising a timer configured to set an operation schedule, wherein the image pickup element, image processing circuit, memory, transmitting circuit and antenna operate in accordance with the operation schedule set by the timer.

4. A capsule type endoscope comprising:

a capsule body;

an illuminating unit provided in the capsule body and configured to illuminate an inside of a living body;

an image pickup element provided in the capsule body and configured to take images in a living body illuminated by the illuminating unit and to generate signals from the images taken;

a processing circuit provided in the capsule body and configured to process the signals, thereby to generate image signals;

a memory provided in the capsule body and configured to store the image signals;

a transmitting circuit provided in the capsule body and configured to read the image signals from the memory and convert the image signals to signals to be transmitted;

an antenna configured to transmit the transmit signals from the living body, without using wires;

a timer configured to set an operation schedule, wherein the image pickup element, mane processing circuit, memory, transmitting circuit and antenna operate in accordance with the operation schedule set by the timer; and a detecting unit which is held in the capsule body and which detects a position of the capsule body, wherein the detecting unit detects an electromagnetic field emanating from an external plate arranged outside the living body to determine the position of the capsule body, and wherein the operation schedule is set in the timer such that the image pickup element continues to pickup an image only when the capsule type endoscope detects that the detecting unit is located near the external plate.

5. A capsule type endoscope according to claim 4, wherein the external plate is a magnet plate.

6. A capsule type endoscope according to claim 4, wherein the external plate is a conductive plate.

7. A capsule type endoscope comprising:

a capsule body;

an illuminating unit provided in the capsule body and configured to illuminate an inside of a living body;

an image pickup element provided in the capsule body and configured to take images in a living body illuminated by the illuminating unit and to generate signals from the images taken;

a processing circuit provided in the capsule body and configured to process the signals, thereby to generate image signals;

a memory provided in the capsule body and configured to store the image signals;

a transmitting circuit provided in the capsule body and configured to read the image signals from the memory and convert the image signals to signals to be transmitted, and an antenna configured to transmit the signals from the living body, without using wires, wherein the illuminating unit and the image pickup element are provided in a front end portion, so that a center of mass of the capsule type endoscope is in the front end portion of the capsule type endoscope.

8. A capsule type endoscope comprising:

a capsule body;

an illuminating unit provided in the capsule body and configured to illuminate an inside of a living body;

an image pickup element provided in the capsule body and configured to take images in a live body illuminated by the illuminating unit and to generate signals from the images taken;

a processing circuit provided in the capsule body and configured to process the signals, thereby to generate image signals;

a memory provided in the capsule body and configured to store the image signals;

a transmitting circuit provided in the capsule body and configured to read the image signals from the memory and convert the image signals to signals to be transmitted;

an antenna configured to transmit the transmit signals from the living body, without using wires; and a timer configured to set an operation schedule, wherein the image pickup element, image processing circuit, memory, transmitting circuit and antenna operate in accordance with the operation schedule set by the timer;

wherein the illuminating unit and the image pickup element are provided in a front end portion of the capsule type endoscope, so that a center of mass is in the front end portion.

9. A method for photographing an inside of a living body by means of a capsule type endoscope swallowed by a subject, the capsule type endoscope including a capsule main body, a photographing device incorporating an image pickup element and an illuminating unit, the method comprising the steps of:

illuminating the inside of the living body with the illuminating unit, photographing, by the image pickup element in the photographing device, the inside of the living body illuminated by the illuminating unit, and generating an image pickup signal, processing the image pickup signal and generating an image signal;

storing the image signal in a memory provided in the capsule main body;

reading the image signal from the memory, and converting the image signal to a signal to be transmitted;

wirelessly transmitting the signal to be transmitted to an outside of the living body via an antenna provided in the capsule main body; and detecting a position of the capsule main body by means for detecting a position of the capsule main body, and transferring the capsule type endoscope into an image taking mode in which an image taking rate of the image pickup element is lowered in accordance with information on the position.

10. A method for photographing an inside of a living body by means of a capsule type endoscope swallowed by a subject, the capsule type endoscope including a capsule main body, a photographing device incorporating an image pickup element and an illuminating unit, the method comprising the steps of;

illuminating the inside of the living body with the illuminating unit, detecting an external plate, starting photographing, by the image pickup element in the capsule main body, the inside of the living body illuminated by the illuminating unit, and generating an image pickup signal, processing the image pickup signal and generating an image signal;

storing the image signal in a memory provided in the capsule main body; and terminating the photographing when the external plate is not detected, reading the image signal from the memory, and starting wirelessly transmitting the image signal to outside of the living body.

* * * * *

UNITED STATES PATENT AND TRADEMARK OFFICE
CERTIFICATE OF CORRECTION

PATENT NO. : 6,939,292 B2  
APPLICATION NO. : 10/173998  
DATED : September 6, 2005  
INVENTOR(S) : Hitoshi Mizuno Page 1 of 1

It is certified that error appears in the above-identified patent and that said Letters Patent is hereby corrected as shown below:

Column 9, Line 17, Claim 1:

"image signals to signals to be" should read -- image signals to be --

Column 10, Line 5, Claim 3:

"image signals to signals to be" should read -- image signals to be --

Column 10, Line 10, Claim 4:

"mane processing" should read -- image processing --

Column 10, Line 43, Claim 7:

"image signals to signals to be" should read -- image signals to be --

Column 10, Line 66, Claim 8:

"image signals to signals to be" should read -- image signals to be --

Signed and Sealed this

Twenty-eighth Day of November, 2006

JON W. DUDAS  
*Director of the United States Patent and Trademark Office*